(12) United States Patent
Morishita et al.

(10) Patent No.: US 8,021,295 B2
(45) Date of Patent: Sep. 20, 2011

(54) ENDOSCOPE SYSTEM AND OBSERVATION METHOD USING THE SAME

(75) Inventors: Koki Morishita, Tokyo (JP); Akira Hasegawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 1242 days.

(21) Appl. No.: 11/710,808

(22) Filed: Feb. 26, 2007

(65) Prior Publication Data
US 2007/0213588 A1 Sep. 13, 2007

(30) Foreign Application Priority Data

Feb. 28, 2006 (JP) ................................. 2006-051915

(51) Int. Cl.
*A61B 1/015* (2006.01)
*A61B 1/06* (2006.01)
(52) U.S. Cl. .................... 600/159; 600/178; 600/476
(58) Field of Classification Search .................. 600/109, 600/111, 113, 153, 156–160, 166, 168, 170, 600/171, 178, 181, 476, 478
See application file for complete search history.

(56) References Cited

U.S. PATENT DOCUMENTS

| 6,293,911 | B1 * | 9/2001 | Imaizumi et al. | 600/160 |
|---|---|---|---|---|
| 6,389,307 | B1 * | 5/2002 | Abela | 600/478 |
| 2004/0092825 | A1 * | 5/2004 | Madar et al. | 600/473 |
| 2004/0210113 | A1 * | 10/2004 | Hasegawa | 600/181 |
| 2005/0200842 | A1 * | 9/2005 | Bonningue et al. | 356/241.1 |

FOREIGN PATENT DOCUMENTS

| JP | 11-155812 | 6/1999 |
|---|---|---|
| JP | 2003-510121 | 3/2003 |
| JP | 2004-377 | 1/2004 |
| JP | 2005-46361 | 2/2005 |
| JP | 2005-342032 | 12/2005 |

OTHER PUBLICATIONS

Haringsma, J. and Tytgat, G.N.J., "Fluorescence and autofluorescence", 1999, Bailliere's Clinical Gastroenterology, vol. 13, No. 1, pp. 1-10.*
J. C. Kennedy, et al., "Photodynamic Therapy With Endogenous Protoporphyrin IX: Basic Principles and Present Clinical Experience," Journal of Photochemistry and Photobiology, B: Biology, 6 (1990) pp. 143-148.

* cited by examiner

*Primary Examiner* — John P Leubecker
(74) *Attorney, Agent, or Firm* — Scully, Scott, Murphy & Presser, P.C.

(57) ABSTRACT

An endoscope system and an observation method using the same includes an agent dispensing portion for dispensing towards an acquisition object a fluorescent agent; a light source portion for emitting excitation light for exciting the fluorescent agent and irradiation light having different spectral characteristics from the excitation light; an optical system for transmitting the excitation light and the irradiation light towards the acquisition object; image-acquisition means, disposed at a portion that is inserted inside a body cavity and capable of acquiring fluorescence excited from the acquisition object by the excitation light, and light in a different wavelength band, which is excited from the acquisition object by the irradiation light; and control means for controlling the agent-dispensing means so that the acquisition object is irradiated with the irradiation light before the fluorescent agent is spouted out towards the acquisition object and for synchronizing at least the operation for spouting the fluorescent agent from the agent dispensing portion with the irradiation of the excitation light.

7 Claims, 11 Drawing Sheets

ENDOSCOPE SYSTEM AND OBSERVATION METHOD USING THE SAME

BACKGROUND OF THE INVENTION

1. Field of the Invention

The present invention relates to an endoscope system and to an observation method using the same.

This application is based on Japanese Patent Application No. 2006-051915, the content of which is incorporated herein by reference.

2. Description of Related Art

In endoscopy, observation of fluorescence images can give different information about a living organism from reflection images, and it is therefore beneficial in the diagnosis and observation of diseases.

For example, if a fluorescent probe that reacts with a substance originating in a diseased area to change from a non-fluorescent substance to a fluorescent substance is administered, it is possible to observe the concentration distribution of the substance originating from the disease by examining the fluorescence image.

By observing autofluorescence, that is, fluorescence originating in the living organism itself, it is possible to observe changes in the living organism and to monitor the disease.

At the same time, useful information different from that in fluorescence images is also contained in reflection images.

That is, using a reflection image, it is possible to observe the density of blood vessels, accumulation, and so forth, which allows information related to a disease, such as inflammation, to be obtained.

There are known fluorescent dyes for in vivo visualization of disease sites such as tumors and cancer tissue with high sensitivity; they act as fluorescent probes which bind with substances originating in diseased areas and emit fluorescence. A method using 5-aminolevulinic acid, which is exogenous substance, has already been employed in clinical applications (for example, see Kennedy, J. C. et al.: J Photochem Photobiol B 6:143, 1990).

However, oral administration or administration by intravenous injection or the like, as typified by the method using 5-aminolevulinic acid, requires a large amount of the agent, and therefore has the drawback that it consumes a large amount of fluorescent material, which is generally expensive.

In addition, since it is administered to the whole body, it takes time to accumulate in the tumor site. For example, because there is a time delay for accumulation at various sites in the digestive system, there is a problem in that it is not possible to observe it at the desired instant.

Furthermore, because the intensity of the fluorescence is very weak, there is a problem in that the quality of the fluorescence image tends to deteriorate due to noise and so forth.

BRIEF SUMMARY OF THE INVENTION

The present invention has been conceived in light of the circumstances described above, and an object thereof is to provide an endoscope system and an observation method using the same in which a fluorescent dye/probe that can quickly identify the presence of disease is efficiently applied in a living organism and optically detected to acquire clear fluorescence images.

To realize the object described above, the present invention provides the following solutions.

According to a first aspect, the present invention provides an endoscope system, at least a portion of which is inserted inside the body cavity of a living organism for acquiring images of an acquisition object inside the body cavity, comprising a agent-dispensing portion for dispensing towards the acquisition object a fluorescent agent that reacts with a specific substance inside the acquisition object or that accumulates inside the acquisition object; a light-source portion for emitting excitation light for exciting the fluorescent agent and irradiation light having different spectral characteristics from the excitation light; an optical system for transmitting the excitation light and the irradiation light from the light-source portion towards the acquisition object; an image-acquisition portion, disposed in the portion that is inserted inside the body cavity and capable of acquiring fluorescence excited from the acquisition object by the excitation light, and light in a different wavelength band from the fluorescence, irradiated from the acquisition object by the irradiation light; and a control portion for controlling the operation of the agent dispensing portion so that the acquisition object is irradiated with the irradiation light before the fluorescent agent is spouted out towards the acquisition object.

In the first aspect of the present invention described above, of the light irradiated from the acquisition object, the light in a different wavelength band from the fluorescence may be visible-band reflected light among reflected irradiation light.

In the first aspect of the present invention described above, of the light irradiated from the acquisition object, the light in the different wavelength band from the fluorescence may be visible-band light which a substance originally present inside the acquisition object emits upon being excited by the irradiation light.

In the first aspect of the present invention described above, the fluorescent agent may include an esterase-sensitive fluorescent probe having a fluorescein structure or a fluorescent probe having a cyanine-based compound.

The first aspect of the present invention described above may further comprise a cleaning-water dispensing portion for dispensing cleaning water towards the acquisition object to clean the surface of the acquisition object, wherein the control portion controls the operation of the cleaning-water dispensing portion so that irradiation of the acquisition object with the irradiation light is completed after cleaning of the surface of the acquisition object by the cleaning-water dispensing portion.

According to a second aspect, the present invention provides an endoscope system, at least a portion of which is inserted inside a body cavity of a living organism for acquiring images of an acquisition object inside the body cavity, comprising agent dispensing means for dispensing towards the acquisition object a fluorescent agent that reacts with a specific substance inside the acquisition object or that accumulates in the acquisition object; a light-source portion for emitting excitation light for exciting the fluorescent agent and irradiation light having different spectral characteristics from the excitation light; an optical system for transmitting the excitation light and the irradiation light from the light source portion towards the acquisition object; image-acquisition means, disposed in the portion that is inserted inside the body cavity and capable of acquiring fluorescence excited from the acquisition object by the excitation light, and light in a different wavelength band from the fluorescence, excited from the acquisition object by the irradiation light; and control means for controlling the operation of the agent dispensing means so that the acquisition object is irradiated with the irradiation light before the fluorescent agent is spouted out towards the acquisition object.

According to a third aspect, the present invention provides an observation method using an endoscope system, at least a portion of which is inserted inside a body cavity of a living organism for acquiring images of an acquisition object inside the body cavity, comprising a step of dispensing towards the acquisition object a fluorescent agent that reacts with a specific substance inside the acquisition object or that is accumulated in the acquisition object; a step of radiating towards the acquisition object excitation light for exciting the spouted fluorescent agent in the acquisition object; a step of acquiring fluorescence excited from the acquisition object by the excitation light using an image-acquisition portion provided in the portion of the endoscope system that is inserted inside the body cavity; and a step of acquiring, with the image-acquisition portion, reflected irradiation light which is reflected at the acquisition object when the acquisition object is irradiated with the irradiation light having different spectral characteristics from the excitation light, before the fluorescent agent is spouted out towards the acquisition object.

The present invention affords an advantage in that a fluorescent dye/probe that selectively dyes cells and tissue of cancer/tumors to differentiate them from normal cells and tissue and that can rapidly identify the presence of disease is efficiently applied in a living organism and optically detected to obtain clear fluorescent images.

DETAILED DESCRIPTION OF THE INVENTION

An endoscope system 1 according to a first embodiment of the present invention will be described below with reference to FIGS. 1 to 6.

Figure 1:
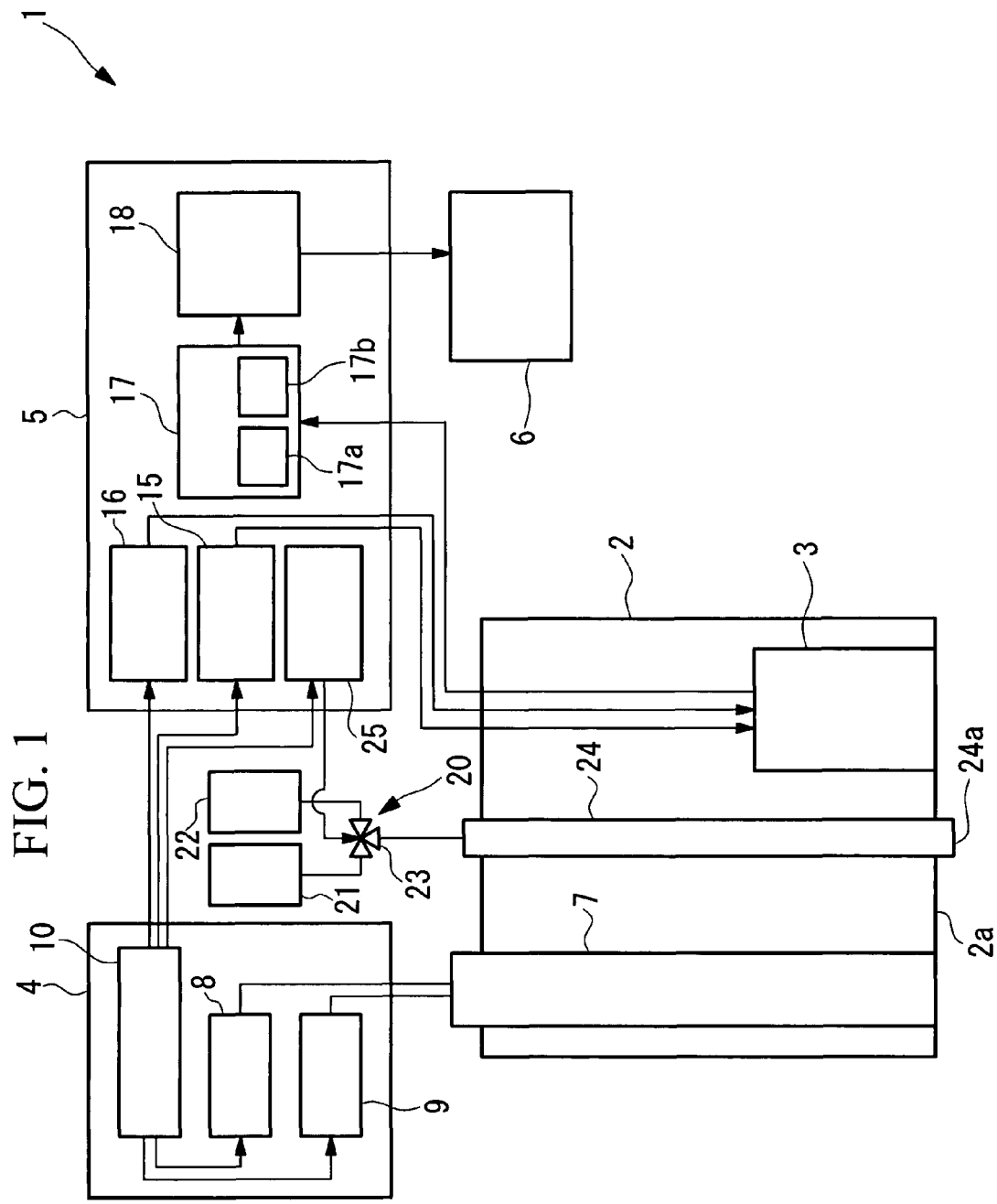
FIG. 1 is a block diagram showing the overall configuration of an endoscope system according to a first embodiment of the present invention.

As shown in FIG. 1, the endoscope system 1 according to this embodiment includes an insertion portion 2 for insertion into a body cavity of a living organism, an image-acquisition unit (image-acquisition portion) 3 disposed inside the insertion portion 2, a light-source unit (light-source portion) 4 for emitting a plurality of types of light, a liquid-delivery unit 20 (agent dispensing portion, cleaning-water dispensing portion) for supplying liquid to be spouted out from the tip 2a of the insertion portion 2, a control unit (control portion) 5 for controlling the image-acquisition unit 3, the light-source unit 4, and the liquid-delivery unit 20, and a display unit (output portion) 6 for displaying images acquired by the image-acquisition unit 3.

The insertion portion 2 has extremely narrow outer dimensions, allowing it to be inserted inside the body cavity of the living organism. The insertion portion 2 includes the image-acquisition unit 3 and a light guide (light-guiding optical system) 7 for transmitting light from the light-source unit 4 to a tip 2a.

The light-source unit 4 includes an illumination light source 8 which emits illumination light (irradiation light) for illuminating an examination target inside the body cavity to obtain reflected light returning after reflection at the examination target, an excitation light source 9 which emits excitation light for irradiating the examination target inside the body cavity to generate fluorescence upon exciting a fluorescent material present inside the examination target, and a light-source control circuit 10 for controlling these light sources 8 and 9.

The illumination light source 8 is, for example, a combination of a xenon lamp and a bandpass filter (which are not shown in the drawing). The 50%-transmittance region of the bandpass filter is from 420 nm to 450 nm. In other words, the illumination light source 8 emits illumination light in the wavelength band of 420 nm to 450 nm.

The excitation light source 9 is, for example, a semiconductor laser emitting excitation light with a peak wavelength of 490±5 nm (or an argon laser emitting excitation light of 488±5 nm). The excitation light of this wavelength can excite the esterase-sensitive fluorescent probe having a fluorescein structure.

The chemical formula of the esterase-sensitive fluorescent probe having a fluorescein structure is as shown in the general formula (1) below.

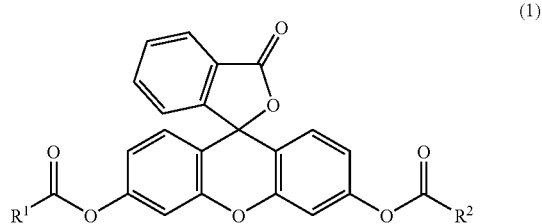

In the formula $R^1$ and $R^2$ indicate $C_1$-$C_4$ alkyl groups which may independently have substituents, $C_2$-$C_4$ alkenyl groups which may have substituents, $C_2$-$C_4$ alkynyl groups which may have substituents, aryl groups which may have substituents, or heteroaryl groups which may have substituents. Accordingly, a selective fluorescent staining agent for tumor cells or tumor tissue including a compound represented by general formula (I) is provided.

According to a preferable aspect, the invention described above provides the fluorescent staining agent in which $R^1$ and $R^2$ are independent $C_1$-$C_3$ alkyl groups, $C_2$-$C_4$ alkenyl groups, aryl groups, or heteroaryl groups; the fluorescent staining agent in which $R^1$ and $R^2$ are independent $C_1$-$C_4$ alkyl groups or $C_2$-$C_4$ alkenyl groups; the fluorescent staining agent in which $R^1$ and $R^2$ are independent $C_1$-$C_3$ alkyl groups or $C_2$-$C_3$ alkenyl groups; and the fluorescent staining agent in which $R^1$ and $R^2$ are —CH=CH$_2$.

In general formula (1), it is possible to use a monocyclic or condensed multicyclic aromatic hydrocarbon as the aryl group. Examples of such aryl groups include phenyl groups, napthyl groups and so forth. As the heteroaryl group, it is possible to use a monocyclic or condensed multicyclic aromatic group including one or two or more heteroatoms. Examples of such heteroatoms include nitrogen atoms, oxygen atoms, sulfur atoms, or the like. If the heteroaryl group includes two or more heteroatoms, those heteroatoms may be of the same type or of different types. Possible examples of such heteroaryl groups include furyl groups, thienyl groups, imidazolyl groups, pyrimidyl groups, or the like.

Representative examples of the compounds represented by general formula (1) include a compound in which $R^1$ and $R^2$ are methyl groups (fluorescein diacetete: FDA); compounds in which $R^1$ and $R^2$ are vinyl groups (fluorescein diacrylate: FDAcr); compounds in which $R^1$ and $R^2$ are ethyl groups (FDP); compounds in which $R^1$ and $R^2$ are n-propyl groups (FDB); compounds in which $R^1$ and $R^2$ are n-butyl groups (FDC); compounds in which $R^1$ and $R^2$ are phenyl groups (FDBz); and compounds in which $R^1$ and $R^2$ are 2-furyl groups. However, the esterase-sensitive fluorescent probe used in the present invention is not limited to the representative examples mentioned above.

The light-source control circuit 10 is configured to alternately turn on and off the illumination light source 8 and the excitation light source 9 at a predetermined timing according to the timing chart to be described later.

Figure 2:
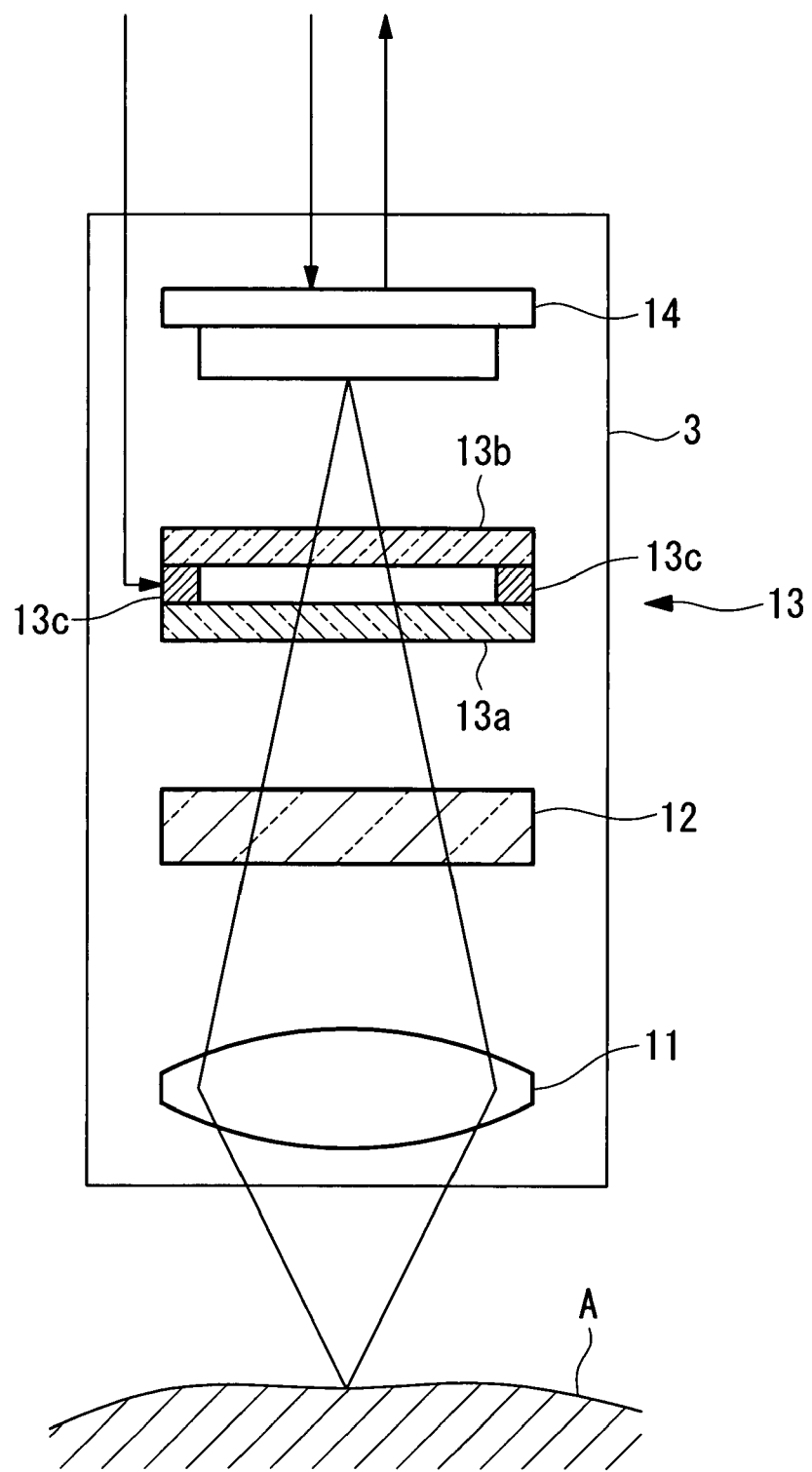
FIG. 2 is a diagram showing, in outline, the configuration of an image-acquisition unit of the endoscope system in FIG. 1.

As shown in FIG. 2, the image-acquisition unit 3 includes an image-acquisition optical system 11 for focusing light incident from the examination target A, a excitation-light-cutting filter 12 for blocking the excitation light incident from the examination target A, a tunable spectral device (tunable spectral portion) 13 whose spectral characteristics can be changed by the operation of the control unit 5, and an image-acquisition device 14 for acquiring the light focused by the image-acquisition optical system 11 and converting it to an electrical signal.

The tunable spectral device 13 is an etalon-type optical filter including two planar optical members 13a and 13b, which are disposed in parallel with a gap therebetween and in which reflective films are disposed on opposing faces thereof, and an actuator 13c for changing the gap between the optical members 13a and 13b. The actuator 13c is a piezoelectric device, for example. This tunable spectral device 13 can change the wavelength band of the light transmitted therethrough by changing the size of the gap between the optical members 13a and 13b by operating the actuator 13c.

Figure 3:
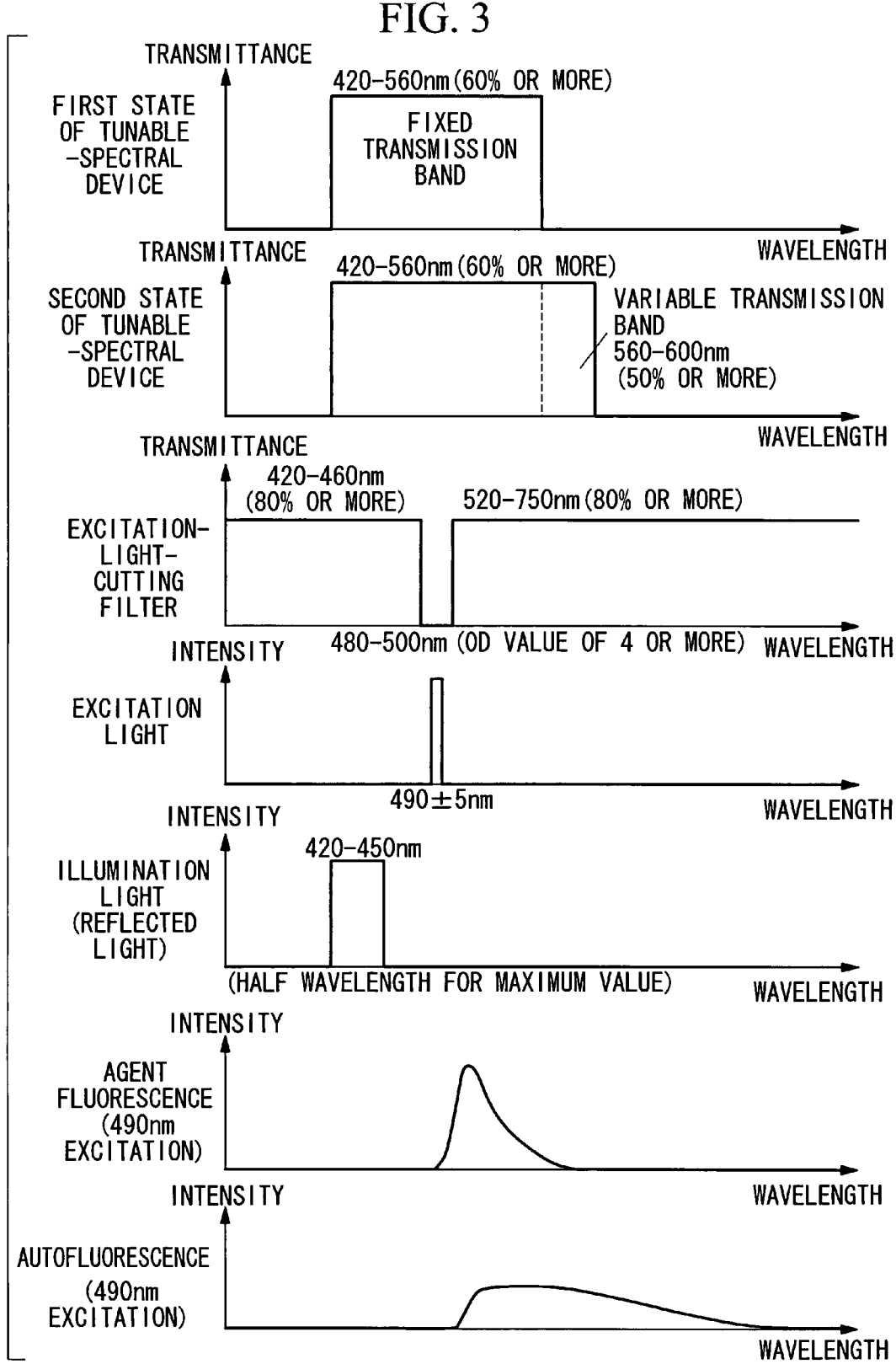
FIG. 3 is a diagram showing transmittance characteristics of each optical component constituting the endoscope system in FIG. 1, as well as the wavelength characteristics of irradiation light and fluorescence.

More specifically, as shown in FIG. 3, the tunable spectral device 13 has a transmittance-versus-wavelength characteristic exhibiting two transmission bands, that is, one fixed transmission band and one variable transmission band. The fixed transmission band always transmits incident light, regardless of the state of the tunable spectral device 13. The transmittance characteristics of the variable transmittance band change according to the state of the tunable spectral device 13.

In this embodiment, the tunable spectral devices 13 has a variable transmittance band in the red wavelength region (for example, the wavelength band of 560 nm to 600 nm). The tunable spectral device 13 changes between two states according to a control signal from the control unit 5.

In the first state of the tunable spectral device 13, the transmittance in the variable transmittance band is sufficiently reduced compared to the second state, to transmit the agent fluorescence. In the second state of the tunable spectral device 13, the transmittance in the variable transmittance band is increased to 50% or more to transmit reflected illumination light. As shown in FIG. 3, in the first state, by sufficiently reducing the transmittance in the variable transmittance band compared to the second state, the tunable spectral device 13 can block living-organism autofluorescence generated in the variable transmittance band, which acts as noise during acquisition of the agent fluorescence, and allows agent fluorescence generated mainly in the fixed fluorescence band to be transmitted. As shown in FIG. 3, in the second state, by setting the fixed transmittance band from 420 nm to 560 nm and the variable transmittance band from 560 nm to 600 nm, the tunable spectral device 13 can transmit blue, green, and red, which are necessary for RGB color observation.

As shown in FIG. 3, for example, the illumination light is from 420 nm to 450 nm, which reflects information about the blood vessels. As the illumination light, it is also possible to use red (from 580 nm to 590 nm), where the light absorption characteristics of the living organism are low, reflecting the surface shape more than blue.

The fixed transmission band of the tunable spectral device 13 is located, for example, in the region from 420 nm to 560 nm. The transmittance of the fixed transmission band of the tunable spectral device 13 is fixed at 60% or higher.

The fixed transmittance band is located in the wavelength band including the wavelength of reflected light for the illumination light. Accordingly, the tunable spectral device 13 can transmit the reflected light towards the image-acquisition device 14 in both the first state and the second state.

The transmittance characteristics of the excitation-light-cutting filter 12 have a transmittance of 80% or more in the wavelength band 420 nm to 470 nm, an OD value of 4 or more (=a transmittance of $1\times10^{-4}$ or less) in the wavelength band 480 nm to 500 nm, and a transmittance of 80% or more in the wavelength band 520 nm to 750 nm.

As shown in FIG. 1, the control unit 5 includes an image-acquisition-device driving circuit 15 for driving and controlling the image-acquisition device 14, a tunable spectral-device control circuit 16 for driving and controlling the tunable spectral device 13, a valve control circuit 25 which is described later, a frame memory 17 for storing image information acquired by the image-acquisition device 14, and an image-processing circuit 18 for processing the image information stored in the frame memory 17 and outputting it to the display unit 6.

The image-acquisition-device driving circuit 15 and the tunable spectral-device control circuit 16 are connected to the light-source control circuit 10. Accordingly, the image-acquisition device driving circuit 15 and the tunable spectral-device control circuit 16 drive and control the tunable spectral device 13 and the image-acquisition device 14 in synchronization with the switching of the illumination light source 8 and the excitation light source 9 by the light-source control circuit 10.

Figure 4:
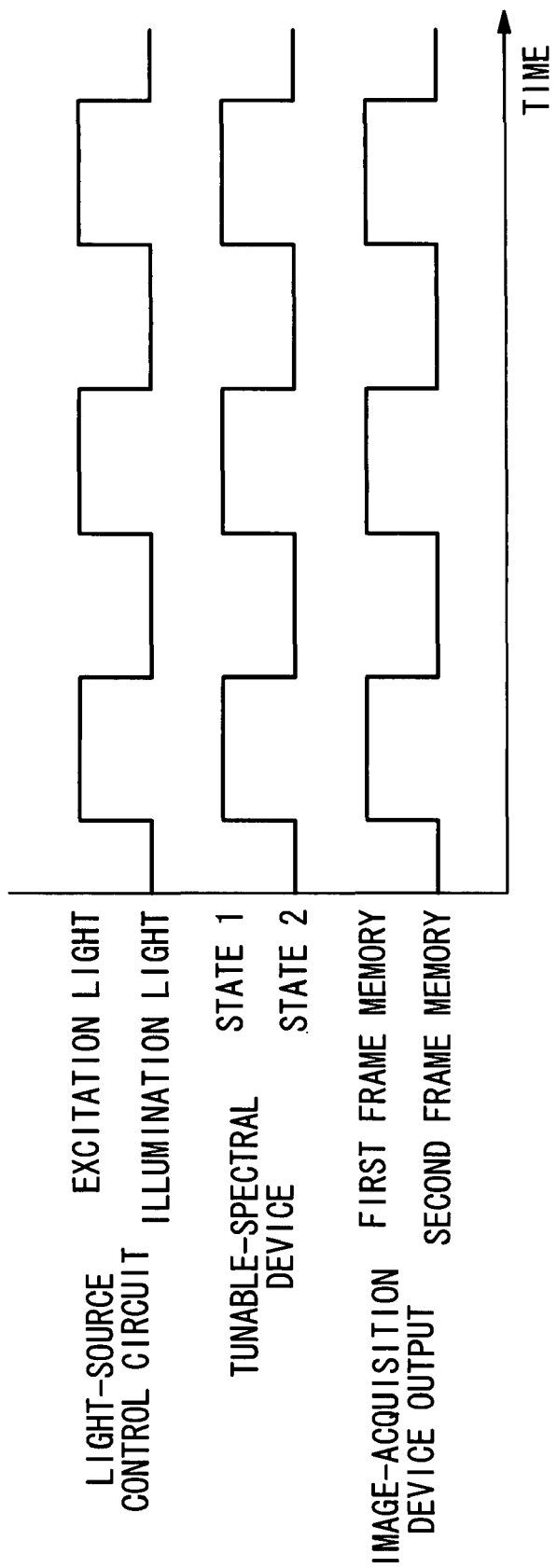
FIG. 4 is a timing chart for explaining the operation of the endoscope system in FIG. 1.

More concretely, as shown in the timing chart in FIG. 4, by operating the light-source control circuit 10, when the excitation light is emitted from the excitation light source 9, the tunable spectral-device control circuit 16 puts the tunable spectral device 13 in the first state, and the image-acquisition-device control circuit 15 outputs image information output from the image-acquisition device 14 to the first frame memory 17a. Also, when the illumination light is emitted from the illumination light source 8, with the tunable spectral-device control circuit 16 having set the tunable spectral device 13 in the second state, the image-acquisition-device driving circuit 15 outputs to a second frame memory 17b the image information output from the image-acquisition device 14.

The image-processing circuit 18, for example, receives from the first frame memory 17a fluorescence image information acquired by irradiating the excitation light and outputs it to the red channel of the display unit 6, and also receives from the second frame memory 17b reflected-light image information acquired by irradiating the illumination light and outputs it to the green channel of the display unit 6.

The liquid-delivery unit 20 includes a first tank 21 for storing cleaning water for cleaning the affected area; a second tank 22 for storing fluorescent dye/probe liquid; a valve 23 for selectively supplying/stopping liquid from these tanks 21 and 22; a liquid-delivery tube 24, connected to the valve 23, for supplying liquid to the tip 2a along the insertion portion 2; and a valve control circuit 25, disposed inside the control unit 5, for controlling the valve 23. The valve 23 is formed, for example, of a three-way valve. An end 24a of the liquid-delivery tube 24 is disposed in the tip 2a of the insertion portion 2, allowing the supplied cleaning water or the fluorescent dye/probe liquid to be applied towards the examination target A. As the liquid-delivery tube 24, it is possible to use a forceps channel provided in the insertion portion 2.

Figure 5:
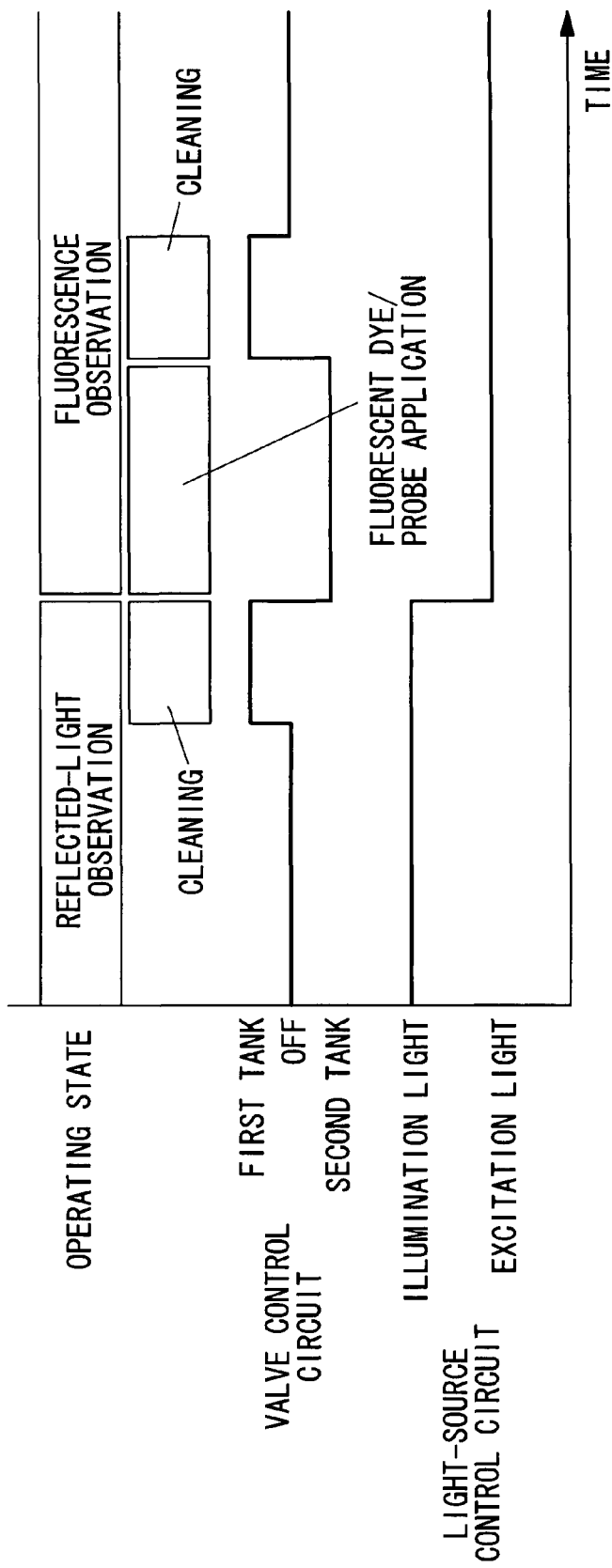
FIG. 5 is a timing chart for explaining the operational states of a valve control circuit in the endoscope system in FIG. 1.

The valve control circuit 25 is connected to the light-source control circuit 10. As shown in FIG. 5, the valve control circuit 25 synchronizes at least the operation for applying the fluorescent dye/probe liquid stored in the second tank 22 with the irradiation of the excitation light from the excitation light source 9.

The operation of the endoscope system 1 according to this embodiment, having such a configuration, will be described below.

To acquire an image of the acquisition object A inside the body cavity of the living organism using the endoscope system 1 according to this embodiment, with a fluorescent agent injected into the body, the insertion portion 2 is inserted into the body cavity so that the tip 2a thereof opposes the acquisition object A in the body cavity. In this state, the light-source unit 4 and the control unit 5 are operated, and by operating the light-source control circuit 10, the illumination light source 8 and the excitation light source 9 are alternately operated to generate illumination light and excitation light, respectively.

The excitation light and the illumination light generated in the light-source unit 4 are transmitted to the tip 2a of the insertion portion 2 via the light guide 7 and are radiated from the tip 2a of the insertion portion 2 towards the acquisition object A.

When the excitation light irradiates the acquisition object A, the fluorescent agent permeating the acquisition object A is excited and emits fluorescence. The fluorescence emitted from the acquisition object A is collected by the image-acquisition optical system 11 of the image-acquisition unit 3, passes through the excitation-light-cutting filter 12, and enters the tunable spectral device 13.

By operating the tunable spectral-device control circuit 16, the tunable spectral device 13 is switched to the first state in synchronization with the operation of the excitation light source 9. Therefore, the tunable spectral device 13 has a sufficiently increased transmittance in a band including the wavelength band of the fluorescence, which allows the incident fluorescence to be transmitted therethrough. In this case, some of the excitation light irradiating the acquisition object A is reflected at the acquisition object A and enters the image-acquisition unit 3 together with the fluorescence. However, because the excitation-light-cutting filter 12 is provided in the image-acquisition unit 3, the excitation light is blocked and can thus be prevented from entering the image-acquisition device 14.

Then, the fluorescence passing through the tunable spectral device 13 enters the image-acquisition device 14, where fluorescence image information is acquired. The acquired fluorescence image information is stored in the first frame memory 17a, is output to the red channel of the display unit 6 by the image processing circuit 18, and is displayed by the display unit 6.

On the other hand, when the illumination light irradiates the acquisition object A, the illumination light is reflected at the surface of the acquisition object A. The illumination light reflected by the acquisition object A is collected by the image-acquisition optical system 11, passes through the excitation-light-cutting filter 12, and enters the tunable spectral device 13. Since the wavelength band of the reflected illumination light is located within the fixed transmission band of the tunable spectral device 13, all of the reflected light entering the tunable spectral device 13 is transmitted therethrough.

Then, the reflected light passing through the tunable spectral device 13 enters the image-acquisition device 14, where reflected-light image information is acquired. The acquired reflected-light image information is stored in the second frame memory 17b, is output to the green channel of the display unit 6 by the image processing circuit 18, and is displayed by the display unit 6.

In this case, by operating the tunable spectral-device control circuit 16, the tunable spectral device 13 is switched to the second state in synchronization with the operation of the illumination light source 8. In other words, because the transmittance of the tunable spectral device 13 in the wavelength band of the fluorescence is low in this case, even though the fluorescence is incident, it is blocked. Accordingly, only the reflected light is acquired by the image-acquisition device 14.

In the endoscope system according to this embodiment, reflected-light observation is carried out before fluorescence observation by operating the light-source control circuit 10 and the valve control circuit 25. In the reflected-light observation, the light-source control circuit 10 operates the illumination light source 8 to irradiate illumination light towards the examination target.

Then, when switching to fluorescence observation from reflected-light observation, before irradiating the excitation light, the valve control circuit 25 switches the valve 23 to the first tank 21 side, with the illumination light source 8 irradiating the illumination light. Accordingly, the cleaning water stored in the first tank 21 is spouted out towards the examination target A from the end 24a of the liquid-delivery tube 24, and the surface of the examination target A is cleaned.

According to this embodiment, because the examination target A is cleaned while the illumination light source 8 irradiates the illumination light in this case, it is possible to easily check the affected area, and it is possible to clean the site where fluorescent dye is to be applied while checking it.

Thereafter, when the excitation light source 9 is operated by the light-source control circuit 10 so that the examination target A is irradiated with the excitation light, the valve control circuit 25 receives a signal from the light-source control circuit 10 to switch the valve 23 to the second tank 22 side. Accordingly, the fluorescent agent stored in the second tank 22 is spouted out towards the examination target A from the end 24a of the liquid-delivery tube 24.

In this case, according to this embodiment, because the site where fluorescence observation is to be carried out is identified by the reflected-light observation performed before the fluorescence observation, it is possible to accurately apply a small amount of the fluorescent dye to the required site. Also, when applying the fluorescent dye, the excitation light source 9 is operated and excitation light is emitted; therefore, even if the fluorescent dye is transparent, it is possible to reliably apply and administer the fluorescent dye locally while checking application conditions.

With the endoscope system 1 according to this embodiment, by reliably applying, under endoscope observation, the esterase-sensitive fluorescent probe to a site suspected of being diseased, it is possible to immediately determine whether or not it is diseased. In this case, it is possible to quickly identify a tumor site using a small amount of the esterase-sensitive fluorescent probe without circulating it through the whole body via the blood, and therefore, it is possible to detect and view it at the instant viewing is desired. In other words, it is possible to minimize the required amount of expensive fluorescent agent, as opposed to oral administration or administration by intravenous injection or the like (involving administration of a large amount of agent), and it is thus possible to reduce the costs involved in examination.

Furthermore, with the endoscope system 1 according to this embodiment, it is possible to provide the user with an image formed by combining the acquired fluorescence image and reflected-light image.

With the endoscope system 1 according to this embodiment, because the tunable spectral device 13 whose optical transmittance characteristics are changed merely by changing the separation between the planar optical members 13a and 13b is used, it is possible to dispose the extremely compact tunable spectral device 13 and the image-acquisition device 14 in the tip 2a of the insertion portion 2. Therefore, with the endoscope system 1 according to this embodiment, it is not necessary to extract the fluorescence or reflected light from the acquisition object A to outside the body using a fiber bundle.

Because the endoscope system 1 described in this embodiment can acquire other images, not only weak fluorescence images which are prone to image-quality degradation due to noise or the like, it is possible to efficiently identify the affected site.

In the endoscope system 1 according to this embodiment, because the state of the tunable spectral device 13 is switched in synchronization with the switching of the plurality of light sources 8 and 9 in the light-source unit 4, it is possible to acquire a plurality of types of light in different wavelength bands using the same image-acquisition device 14. Accordingly, in the endoscope system 1 according to this embodiment, it is not necessary to provide a plurality of image-acquisition optical systems corresponding to the fluorescence and the reflected light. As a result, it is possible to reduce the diameter of the insertion portion 2 in the endoscope system 1 according to this embodiment.

Because of the presence of external light which is transmitted through an organ of the living organism, even though it is inside the body cavity of the living organism, it is particularly important to reduce noise when observing weak light, as in fluorescence observation. In the endoscope system 1 according to this embodiment, by providing the tunable spectral device 13 in the image-acquisition unit 3, it is possible to always block light of wavelengths other than the examination target, even if the wavelength band being observed changes. Therefore, it is possible to acquire superior images with low noise.

In the endoscope system 1 according to this embodiment, the illumination light source 8 generates illumination light in the wavelength band of 420 nm to 450 nm. Because this wavelength band includes the absorption band of hemoglobin, acquiring an image of the reflected light thereof allows to obtain information about the structure and so forth of blood vessels comparatively close to the surface of the living organism to be obtained.

Generally, the effect of scattering in a living organism decreases as the wavelength increases, and it is easy to observe even fluorescence generated deep inside a living organism. However, light with a wavelength of 1 µm or more is decreased due to absorption by water, which makes its observation difficult. Therefore, by using a fluorescent dye which emits fluorescence in the near-infrared band, as in the endoscope system 1 according to this embodiment, it is possible to effectively obtain information about the inside of the living organism, particularly information about disease, such as cancer, originating from the vicinity of mucus membranes.

In the endoscope system 1 according to this embodiment, in the image-acquisition unit 3, the image-acquisition optical system 11, the excitation-light-cutting filter 12, and the tunable spectral device 13 are arranged in this order from the tip 2a of the insertion portion 2. However, the order in which these components are arranged in the endoscope system 1 according to this embodiment is not limited thereto; it is possible to use any arrangement order.

In the endoscope system 1 according to this embodiment, an esterase-sensitive fluorescent probe having a fluorescein structure was used as the fluorescent dye/probe. Instead of this, however, in addition to a compound indicated by general formula (1) above, or instead of a compound indicated by general formula (1) above, it is possible to use a cyanine-based compound, such as a fluorescent probe having a tricarbocyanine structure. This kind of diagnostic product or contrast agent is also provided by the present invention.

Figure 6:
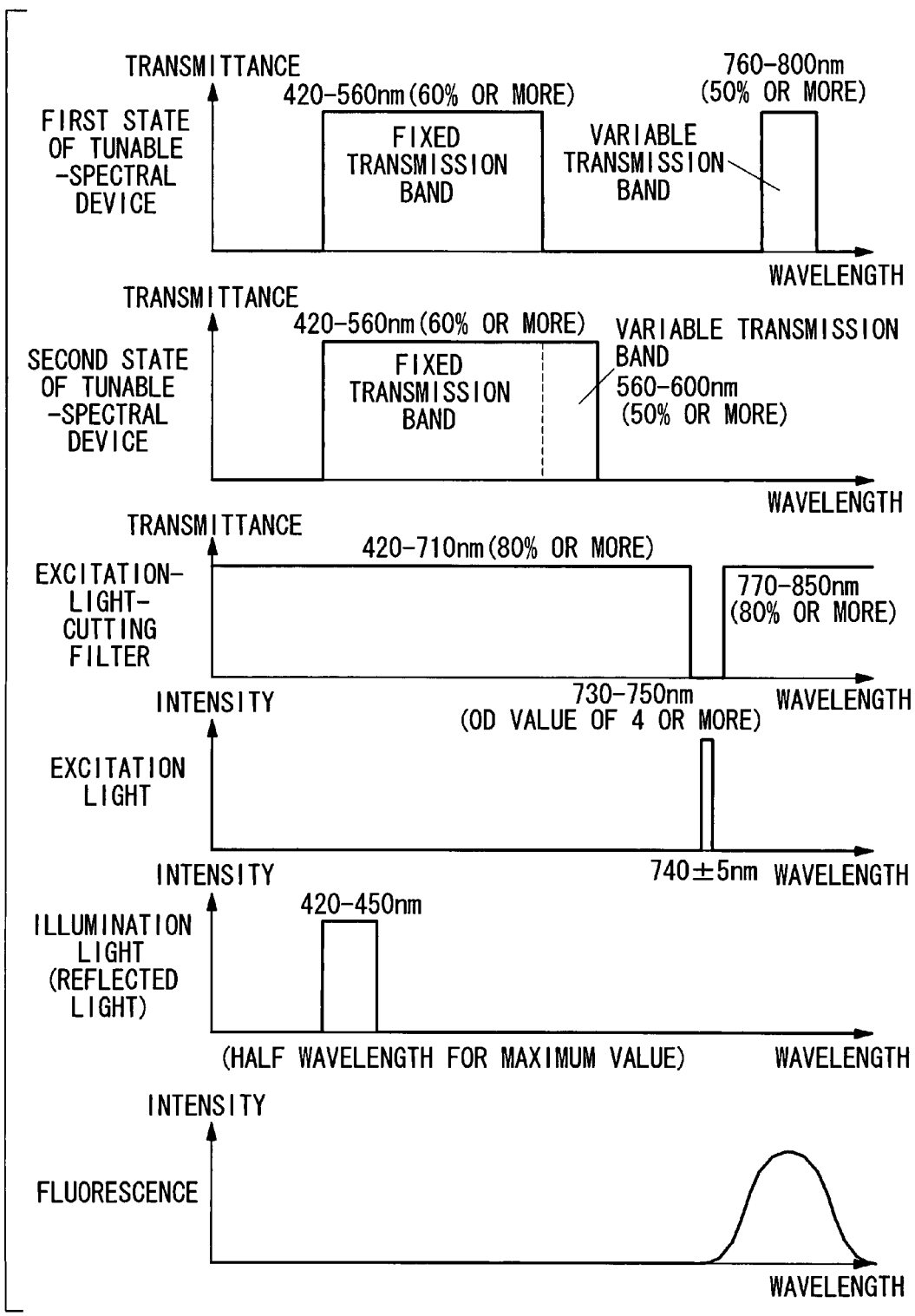
FIG. 6 is a diagram showing transmittance characteristics of each optical component in the endoscope system in FIG. 1 in the case using a cyanine-based fluorescent dye/probe, as well as wavelength characteristics of the irradiation light and fluorescence.

When employing the endoscope system 1 in observation using such a diagnostic agent or contrast agent, as shown in FIG. 6, the tunable spectral device 13 is configured to have a variable transmittance band in a wavelength band (for example, from 760 nm to 800 nm) including the wavelengths of fluorescence (agent fluorescence) emitted by exciting the fluorescent dye/probe with the excitation light. Thus, in this tunable spectral device 13, the first state is a state in which the transmittance in the variable transmission band is increased to 50% or more to transmit the agent fluorescence, and the second state is a state in which the wavelength band of the variable transmission band is shifted, for example, to 560 nm to 600 nm to block the agent fluorescence.

The excitation-light-cutting filter 12 has a transmittance of 80% or more in the wavelength band of 420 nm to 710 nm, an OD value of 4 or more (=transmittance of $1 \times 10^{-4}$ or less) in the wavelength band from 730 nm to 750 nm, and a transmittance of 80% or more in the wavelength band from 770 nm to 850 nm.

The excitation light source 9 is, for example, a semiconductor laser emitting excitation light with a peak wavelength of 740±5 nm. The excitation light of this wavelength can excite the cyanine-based fluorescent dye/probe, such as a fluorescent probe having a tricarbocyanine structure.

By using this type of excitation light source 9, it is possible to realize the same advantages as in the case using the esterase-sensitive fluorescent probe having the fluorescein structure.

In general, when acquiring an image of the interior of a body cavity of a living organism, the brightness of the agent-fluorescence image is extremely small compared to the brightness of the reflected-light image. As a result, it is considered necessary to appropriately adjust the amount of light (exposure level) incident on the image-acquisition device 14 every time switching occurs between reflected-light image observation and agent-fluorescence image observation.

Therefore, in order to operate the fluorescence endoscope system described above according to the brightness of the image measured with the image-acquisition device 14 to adjust the image brightness to approach a predetermined target value set in advance, it is preferable that the control unit 5 switch the irradiation light (excitation light) from the light-source unit 4 and the spectral characteristics of the tunable spectral device 13 and, in addition, perform adjustment of the exposure level of the image-acquisition unit 3 (the image-acquisition device 14) during image acquisition. More concretely, in order to adjust the exposure level, it is preferable to perform one or a plurality of adjustments from among light-level control (adjustment of the emission intensity or the emission time) of the illumination light (excitation light) from the light source 4 and adjustment of the exposure (adjustment of the shutter speed or aperture) of the image-acquisition unit 5 or the gain of the image-acquisition unit 5.

Such adjustment is particularly important when constructing a single image from a plurality of images with very different brightnesses and high-brightness regions (bright regions), such as
when combining a reflected-light image, which is comparatively bright over the entire image, and a agent-fluorescence image, in which the fluorescence region is limited to the region where the agent is applied (administered).

The brightness of the images measured during this image brightness adjustment may be a value measured in a mode where the average value of the entire image or a portion thereof defines the image brightness, that is, an average photometric mode, or it may be a value measured in a mode where the maximum value in the entire image or in a partial region thereof defines the image brightness, that is a peak photometric mode.

Figure 7:
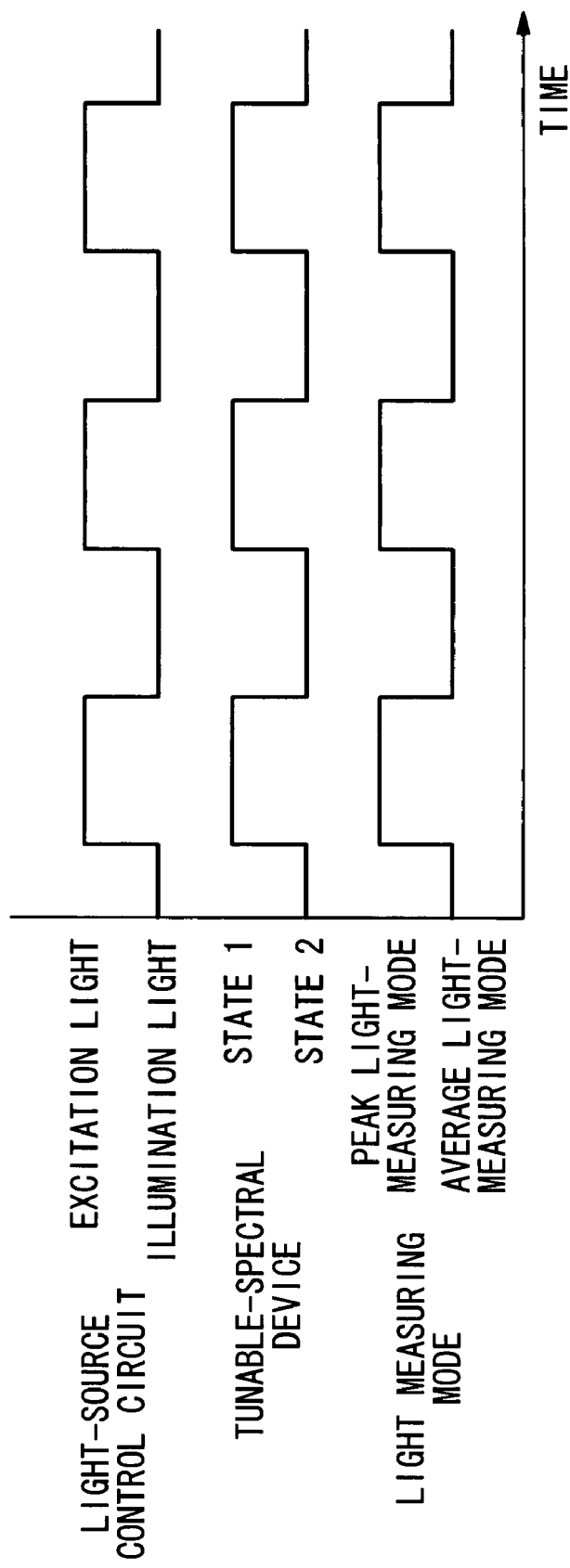
FIG. 7 is a timing chart showing an example of switching of the measurement mode at image acquisition time.

The mode for measuring the image brightness may be controlled in conjunction with the light-source control circuit and the tunable spectral-device control circuit so as to enter the average light-measuring mode during reflected-light image acquisition and the peak light-measuring mode during agent-fluorescence image acquisition, with a predetermined timing according to the timing chart shown in FIG. 7.

The reason for this is that, during reflected-light image acquisition, there are many instances where the subject to be acquired appears in the entire image, forming a comparatively bright region over the entire image, and therefore, the average light-measuring mode is more effective. If peak light measurement were performed on such a reflected-light image, brightness adjustment should be carried out to make the very bright region, for example, reflection from mucus in the living organism, approach a target value, causing the examination target to become dark.

On the other hand, during agent-fluorescence image acquisition, in many instances the generation of fluorescence is limited only to the region where the fluorescent agent is administered (applied), causing most of the image to be a dark region where no fluorescence is generated, forming an image in which the drug fluorescence is visible only in a portion of the image; therefore, the peak light-measurement mode is more effective.

If average light measurement were carried out for such a fluorescence image, brightness adjustment should be carried out to make the dark region occupying most of the image approach the target brightness. Therefore, noise in regions where no fluorescence is generated would be emphasized, producing an image that is difficult to observe.

Next, an endoscope system 1' according to a second embodiment of the present invention will be described below with reference to FIGS. 8 to 10.

In the description of this embodiment, parts having the same configuration as those in the endoscope system 1 according to the first embodiment described above are assigned the same reference numerals, and a description thereof is omitted.

The endoscope system 1' according to this embodiment differs from the endoscope system 1 according to the first embodiment in the configuration of a light-source unit 4' and the transmittance characteristics of the tunable spectral device 13 and the excitation-light-cutting filter 12.

Figure 8:
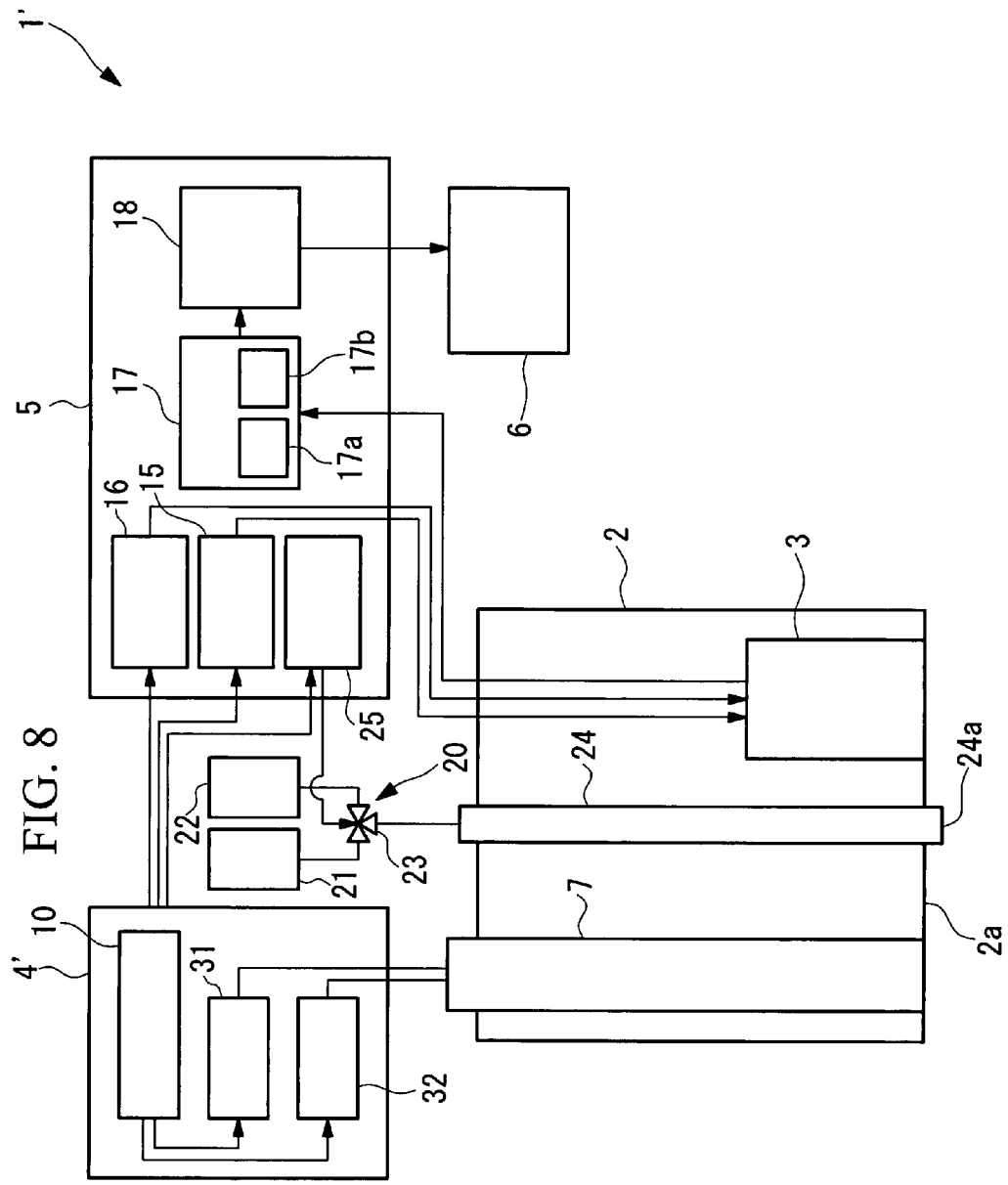
FIG. 8 is a diagram showing the transmittance characteristics of each optical component constituting an endoscope system according to a second embodiment of the present invention, as well as wavelength characteristics of irradiation light and fluorescence.

As shown in FIG. 8, the light-source unit 4' of the endoscope system 1' according to this embodiment includes two excitation light sources 31 and 32.

The first excitation light source 31 is a semiconductor laser emitting first excitation light with a peak wavelength of 490±5 nm. It is possible to excite the esterase-sensitive fluorescent probe having the fluorescein structure with first excitation light which this semiconductor laser emits.

The second excitation light source 32 is a semiconductor laser emitting second excitation light with a peak wavelength of 405±5 nm. It is possible to excite autofluorescence of collagen, NADH, FAD, and the like in the living organism with the second excitation light of this wavelength.

Figure 9:
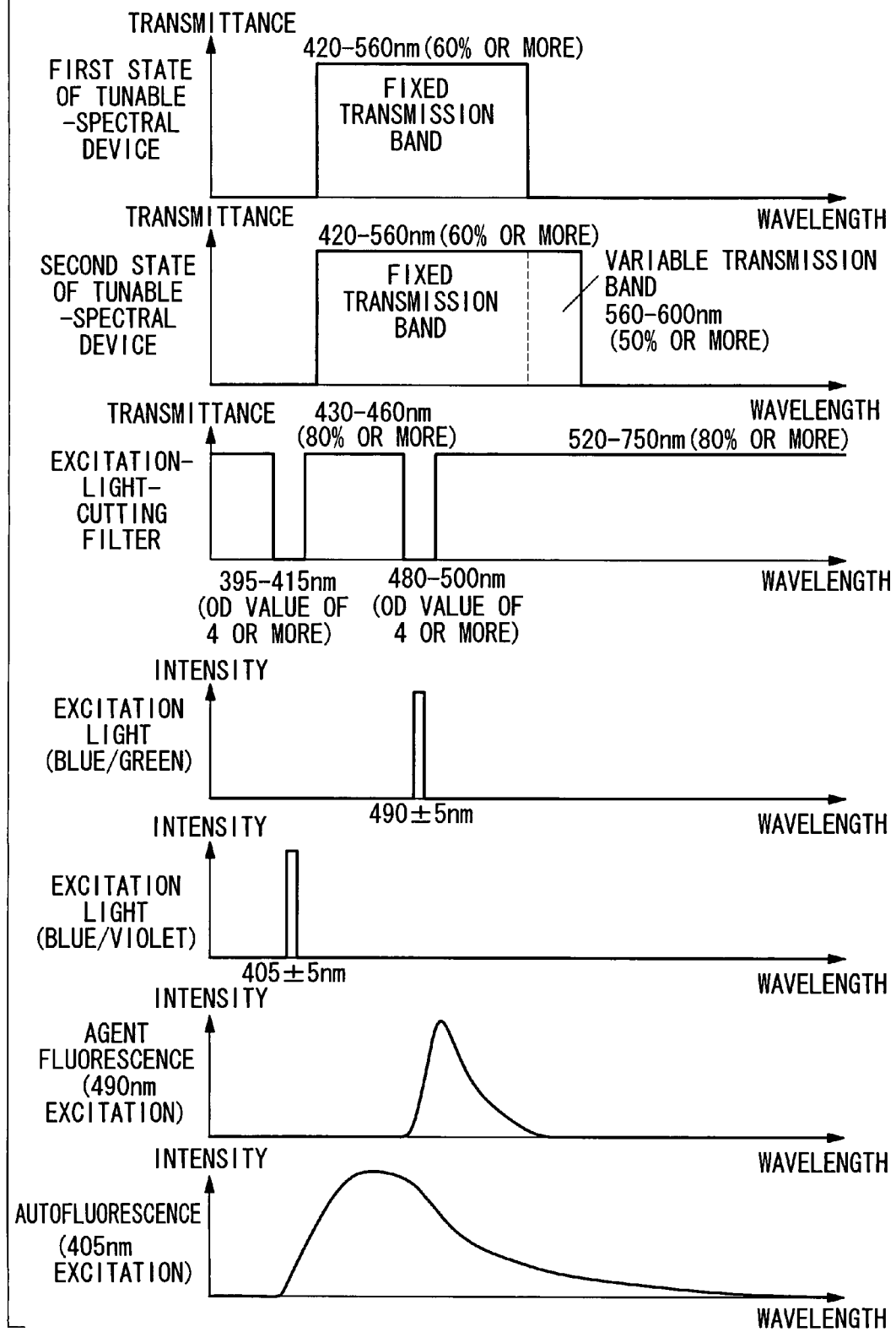
FIG. 9 is a diagram showing transmittance characteristics of each optical component constituting the endoscope system in FIG. 8, as well as wavelength characteristics of irradiation light and fluorescence.
Figure 10:
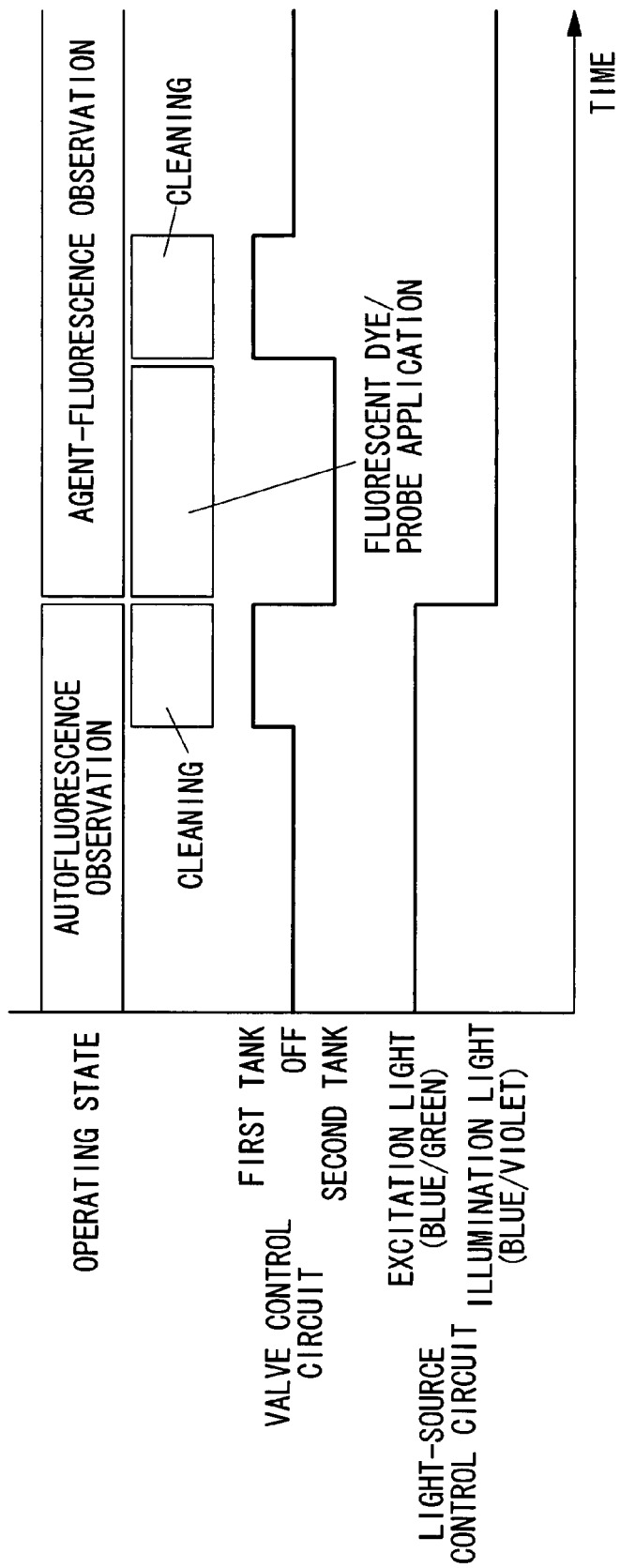
FIG. 10 is a timing chart for explaining operating states of a valve control circuit in the endoscope system in FIG. 8.

As shown in FIG. 9, the tunable spectral device 13 has a high transmittance in the fixed transmission band including the short-wavelength bands of the agent fluorescence and the autofluorescence, and has a variable transmittance band for switching between a first state in which the transmittance in a long-wavelength band of the autofluorescence is low and a second state in which the transmittance in a long-wavelength band of the autofluorescence and in the fixed transmittance band is high.

In the first state, agent fluorescence is transmitted. In the first state, by sufficiently reducing the transmittance in the variable transmittance band compared to the second state, autofluorescence generated in the variable transmittance band, which acts as noise when acquiring agent fluorescence, is blocked.

The fixed transmission band has a transmittance of 60% or more in, for example, a wavelength band of 420 nm to 560 nm. The variable transmittance band has a wavelength band of 560 nm to 600 nm; in the second state, the transmittance is 50% or more, and in the first state, the wavelength band of the variable transmittance band moves inside the fixed transmittance band. The variable transmittance band may have a wavelength band (for example, 620 nm to 660 nm) including the peak wavelength of porphyrin, which is one autofluorescent component.

The transmittance characteristics of the excitation-light-cutting filter 12 exhibit an OD value of 4 or more ($1 \times 10^{-4}$ or less) in the wavelength band of 395 nm to 415 nm, a transmittance of 80% or more in the wavelength band of 430 nm to 460 nm, an OD value of 4 or more ($1 \times 10^{-4}$ or less) in the wavelength band of 480 nm to 500 nm, and a transmittance of 80% or more in the wavelength band of 520 nm to 750 nm.

With the endoscope system 1' according to this embodiment, having such a configuration, when first excitation light is emitted from the first excitation light source 31 by operating the light-source control circuit 10, the operation of the second excitation light source 32 is stopped, and only the first excitation light irradiates the acquisition object A. At this time, because the tunable spectral device 13 is switched to the first state by the tunable spectral-device control circuit 16, in synchronization with the operation of the first excitation light source 31, the agent fluorescence generated in the acquisition object A is transmitted through the tunable spectral device 13 and is acquired by the image-acquisition device 14, and the agent-fluorescence image information is stored in the first frame memory 17a.

On the other hand, when the second excitation light is emitted from the second excitation light source 32 by operating the light-source control circuit 10, the operation of the first excitation light source 31 is stopped, and the acquisition object A is irradiated with only the second excitation light. At this time, because the tunable spectral device 13 is switched to the second state by the tunable spectral-device control circuit 16, in synchronization with the operation of the second excitation light source 32, the autofluorescence generated in the acquisition object A is transmitted through the tunable spectral device 13 and is acquired by the image-acquisition device 14, and autofluorescence image information is stored in the second frame memory 17b.

The agent-fluorescence image information stored in the first frame memory 17a is output by the image processing circuit 18 on, for example, the red channel of the display unit 6 and is displayed by the display unit 6.

On the other hand, the autofluorescence image information stored in the second frame memory 17b is output by the image-processing circuit 18 on, for example, the green channel of the display unit 6 and is displayed by the display unit 6. Accordingly, it is possible to provide the fluorescence endoscope system 1' that presents the user with a combined image formed by combining the agent-fluorescence image and the autofluorescence image and that acquires a plurality of images carrying different types of information.

In the endoscope system 1' according to this embodiment also, the autofluorescence observation is carried out before the agent fluorescence observation by operating the light-source control circuit 10 and the valve control circuit 25. In the autofluorescence observation, the light-source control circuit 10 operates the second excitation light source 32 to irradiate the second excitation light towards the examination target.

Thus, when switching from the autofluorescence observation to the agent-fluorescence observation, before irradiating the first excitation light, the valve control circuit 25 switches the valve 23 to the first tank 21 side, while the second excitation light source 32 radiates second excitation light. Accordingly, the cleaning water stored in the first tank 21 is spouted out from the end 24a of the liquid-delivery tube 24 towards the examination target A, and the surface of the examination target A is cleaned.

In this case, according to this embodiment, because the examination target A is cleaned while the second excitation light source 32 is radiating the second excitation light, it is possible to easily check the affected area based on the autofluorescence, and it is possible to clean the site where the fluorescent dye is to be applied while checking it.

Thereafter, the first excitation light source 31 is operated by the light-source control circuit 10, and the examination target A is irradiated with the first excitation light. Then, the valve control circuit 25 receives a signal from the light-source control circuit 10 for switching the valve to the second tank 22 side. Accordingly, the fluorescent agent stored in the second tank 22 is spouted out from the end 24a of the liquid-delivery tube 24 towards the examination target A.

In this case, according to this embodiment, because the site where fluorescence observation is to be carried out is identified by the autofluorescence performed before the fluorescence observation, it is possible to accurately apply a small amount of fluorescent dye to the required site. Also, when applying the fluorescent dye, the first excitation light source 31 is operated and first excitation light is emitted; therefore, even if the fluorescent dye is transparent, it is possible to reliably apply and administer the fluorescent dye locally while checking application conditions.

Thus, with the endoscope system 1 according to this embodiment, by reliably applying, under endoscope observation, the esterase-sensitive fluorescent probe to a site suspected of being diseased, it is possible to immediately determine whether or not it is diseased. In this case, it is possible to quickly identify the site of a tumor using a small amount of esterase-sensitive fluorescent probe, without circulating it through the entire body via the blood, and it is possible to detect and view it at the instant viewing is desired. In other words, it is possible to minimize the required amount of expensive fluorescent agent, as opposed to oral administration or administration by intravenous injection or the like (involving a administration of a large amount of agent), and it is thus possible to reduce the costs involved in examination.

In the endoscope system 1' according to this embodiment, the esterase-sensitive fluorescent probe having the fluorescein structure is used as the fluorescent dye/probe. Instead of this, however, in the endoscope system 1' according to this embodiment, it is possible to use a cyanine-based fluorescent dye/probe, such as a fluorescent probe having a tricarbocyanine structure.

Figure 11:
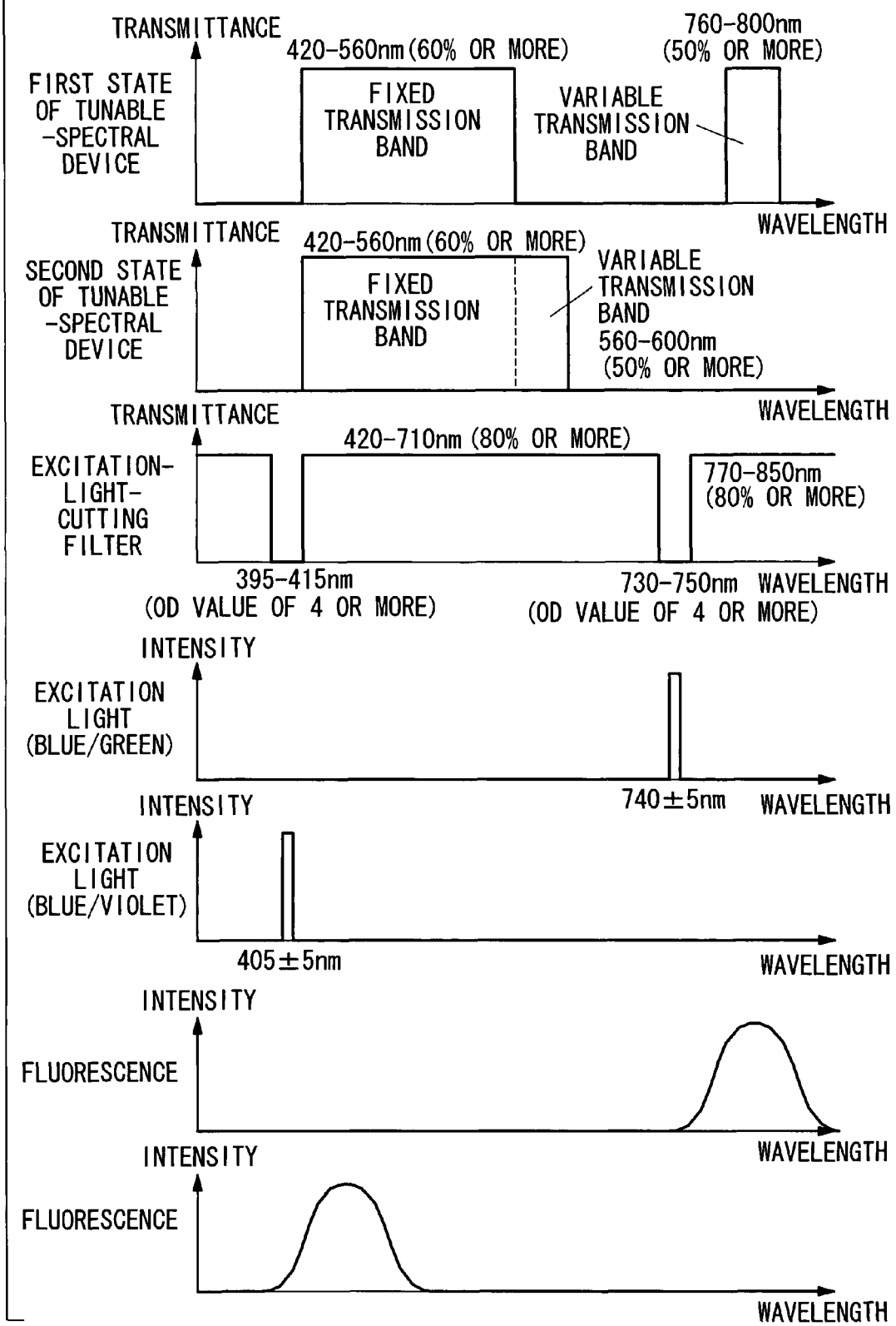
FIG. 11 is a diagram showing transmittance characteristics of each optical component in the endoscope system in FIG. 8 in the case using a cyanine-based fluorescent dye/probe, as well as wavelength characteristics of irradiation light and fluorescence.

In the case where the endoscope system 1' according to this embodiment is employed in observation using such a fluorescent dry/probe, as shown in FIG. 11, the tunable spectral device 13 is configured to have a variable transmittance band in a wavelength band (for example, 760 nm to 800 nm) including the wavelength of the fluorescence (agent fluorescence) emitted by exciting the fluorescent dye/probe with the excitation light. Thus, in this tunable spectral device 13, the first state is a state in which the transmittance in the variable transmission band is increased to 50% or more to transmit the agent fluorescence, and the second state is a state in which the wavelength band of the variable transmission band is shifted, for example, to 560 nm to 600 nm to block the agent fluorescence and transmit the autofluorescence.

The excitation-light-cutting filter 12 has an OD value of 4 or more ($1\times10^{-4}$ or less) in the wavelength band of 395 nm to 415 nm, a transmittance of 80% or more in the wavelength band of 420 nm to 710 nm, an OD value of 4 or more (=transmittance of $1\times10^{-4}$ or less) in the wavelength band of 730 nm to 750 nm, and a transmittance of 80% or more in the wavelength band of 770 nm to 850 nm.

The first excitation light source 31 is, for example, a semiconductor laser emitting excitation light with a peak wavelength of 740±5 nm. The excitation light of this wavelength can excite the cyanine-based fluorescent dye/probe such as a fluorescent probe having a tricarbocyanine structure.

By using this type of first excitation light source 31, it is possible to realize the same advantages as in the case using the esterase-sensitive fluorescent probe having the fluorescein structure.

The fluorescence endoscope systems 1 and 1' of the present invention are not limited to scope-type apparatuses having the image-acquisition portion 14 in the tip of the insertion portion 2 which is inserted inside the body cavity of the living organism. For example, the fluorescence endoscope systems 1 and 1' of the present invention may be applied to capsule-type apparatuses in which a light-source portion, an image-acquisition portion, and tunable spectral means are disposed inside a single housing, and the entire housing can be inserted inside the body cavity of the living organism.

What is claimed is:

1. An endoscope system, at least a portion of which is inserted inside the body cavity of a living organism for acquiring images of an acquisition object inside the body cavity, comprising:
    an agent dispensing portion for dispensing towards the acquisition object a fluorescent agent that reacts with a specific substance inside the acquisition object or that accumulates inside the acquisition object;
    a light source portion for emitting excitation light for exciting the fluorescent agent and irradiation light having different spectral characteristics from the excitation light;
    an optical system for transmitting the excitation light and the irradiation light from the light-source portion towards the acquisition object;
    an image-acquisition portion, disposed in the portion that is inserted inside the body cavity and capable of acquiring fluorescence excited from the acquisition object by the excitation light, and light in a different wavelength band from the fluorescence, excited from the acquisition object by the irradiation light; and
    a control portion for controlling the operation of the agent dispensing portion so that the acquisition object is irradiated with the irradiation light before the fluorescent agent is spouted out towards the acquisition object, and for synchronizing at least the operation for spouting the fluorescent agent from the agent dispensing portion with the irradiation of the excitation light.

2. An endoscope system according to claim 1, wherein, of the light irradiated from the acquisition object, the light in a different wavelength band from the fluorescence is visible-band reflected light among the reflected irradiation light.

3. An endoscope system according to claim 1, wherein, of the light irradiated from the acquisition object, the light in the different wavelength band from the fluorescence is visible-band light which a substance originally present inside the acquisition object emits upon being excited by the irradiation light.

4. An endoscope system according to claim 1, wherein the fluorescent agent includes an esterase-sensitive fluorescent probe having a fluorescein structure or a fluorescent probe having a cyanine-based compound.

5. An endoscope system according to claim 1, further comprising:
    a cleaning-water dispensing portion for dispensing cleaning water towards the acquisition object to clean the surface of the acquisition object,
    wherein the control portion controls the operation of the cleaning-water dispensing portion so that irradiation of the acquisition object with the irradiation light is completed after cleaning of the surface of the acquisition object by the cleaning-water dispensing portion.

6. An endoscope system, at least a portion of which is inserted inside a body cavity of a living organism for acquiring images of an acquisition object inside the body cavity, comprising:
    agent dispensing means for dispensing towards the acquisition object a fluorescent agent that reacts with a specific substance inside the acquisition object or that accumulates in the acquisition object;
    a light-source portion for emitting excitation light for exciting the fluorescent agent and irradiation light having different spectral characteristics from the excitation light;
    an optical system for transmitting the excitation light and the irradiation light from the light source portion towards the acquisition object;
    image-acquisition means, disposed in the portion that is inserted inside the body cavity and capable of acquiring fluorescence excited from the acquisition object by the excitation light, and light in a different wavelength band from the fluorescence, irradiated from the acquisition object by the irradiation light; and
    control means for controlling the operation of the agent dispensing means so that the acquisition object is irradiated with the irradiation light before the fluorescent agent is spouted out towards the acquisition object, and for synchronizing at least the operation for spouting the fluorescent agent from the agent dispensing portion with the irradiation of the excitation light.

7. An observation method using an endoscope system, at least a portion of which is inserted inside a body cavity of a living organism for acquiring images of an acquisition object inside the body cavity, comprising:
    a step of dispensing towards the acquisition object a fluorescent agent that reacts with a specific substance inside the acquisition object or that is accumulated in the acquisition object;
    a step of irradiating towards the acquisition object excitation light for exciting the spouted fluorescent agent in the acquisition object;
    a step of acquiring fluorescence excited from the acquisition object by the excitation light using an image-acquisition portion provided in the portion of the endoscope system that is inserted inside the body cavity; and
    a step of acquiring, with the image-acquisition portion, reflected light reflected at the acquisition object when the acquisition object is irradiated with an irradiation light having different spectral characteristics from the excitation light, before the fluorescent agent is spouted out towards the acquisition object;
    wherein the step of dispensing the fluorescent agent towards the acquisition object is synchronized with the step of irradiating the excitation light towards the acquisition object.

* * * * *